(12) United States Patent
Gorek

(10) Patent No.: US 8,376,940 B2
(45) Date of Patent: Feb. 19, 2013

(54) MINIMALLY INVASIVE RETRACTOR WITH SEPARABLE BLADES AND METHODS OF USE

(75) Inventor: Josef Gorek, Ross, CA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 13/398,139

(22) Filed: Feb. 16, 2012

(65) Prior Publication Data

US 2012/0143011 A1 Jun. 7, 2012

Related U.S. Application Data

(62) Division of application No. 12/396,098, filed on Mar. 2, 2009, now abandoned.

(60) Provisional application No. 61/032,199, filed on Feb. 28, 2008.

(51) Int. Cl.
*A61B 17/70* (2006.01)
*A61B 1/32* (2006.01)

(52) U.S. Cl. .................. 600/206; 606/86 A; 606/279

(58) Field of Classification Search ........... 606/86 A, 606/264–272; 600/204, 206, 208, 212, 235, 600/244
See application file for complete search history.

(56) References Cited

U.S. PATENT DOCUMENTS

| | | | |
|---|---|---|---|
| 3,129,706 A | 4/1964 | Reynolds | |
| 3,486,505 A | 12/1969 | Morrison | |
| 5,242,443 A | 9/1993 | Kambin | |
| 5,431,658 A | 7/1995 | Moskovich | |
| 5,496,321 A | 3/1996 | Puno | |
| 5,545,165 A | 8/1996 | Biedermann | |
| 5,582,577 A | 12/1996 | Lund | |
| 5,797,911 A | 8/1998 | Sherman | |
| 5,902,231 A | 5/1999 | Foley et al. | |
| 5,944,658 A | 8/1999 | Koros et al. | |
| 6,063,088 A | 5/2000 | Winslow | |
| 6,083,225 A | 7/2000 | Winslow et al. | |
| 6,099,547 A | 8/2000 | Gellman et al. | |
| 6,102,951 A | 8/2000 | Sutter | |
| 6,146,385 A | 11/2000 | Torrie et al. | |
| 6,187,000 B1 | 2/2001 | Davison et al. | |
| 6,200,322 B1 | 3/2001 | Branch et al. | |
| 6,206,826 B1 | 3/2001 | Mathews et al. | |
| 6,280,442 B1 | 8/2001 | Barker | |
| 6,358,253 B1 | 3/2002 | Torrie et al. | |
| 6,360,750 B1 | 3/2002 | Gerber et al. | |
| 6,478,800 B1 | 11/2002 | Fraser et al. | |
| 6,485,494 B1 | 11/2002 | Haider | |
| 6,530,926 B1 | 3/2003 | Davison | |
| 6,530,929 B1 | 3/2003 | Justis et al. | |
| 6,616,605 B2 | 9/2003 | Wright et al. | |
| 6,652,533 B2 | 11/2003 | O'Neil | |
| 6,669,729 B2 | 12/2003 | Chin | |

(Continued)

FOREIGN PATENT DOCUMENTS

WO WO 2007/084641 7/2007

*Primary Examiner* — Ellen C Hammond
(74) *Attorney, Agent, or Firm* — Carter, DeLuca, Farrell & Schmidt, LLP

(57) ABSTRACT

A device, system and method for orthopedic spine surgery using a screw-based retractor, are disclosed herein and allows for access to the spine through a minimally or less invasive approach. The retractor device is designed to be coupled to a pedicle screw and then to have opposed arms of the retractor spread apart to open the wound proximally. The retractor is removed by separating the opposed blades to allow the retractor portions to be pulled out of the wound. The retractor is intended to be made of a flexible metal material, sterile packaged and disposable after one use. A system and method for using the retractor and performing a minimally invasive spine surgical procedure are also disclosed.

8 Claims, 6 Drawing Sheets

U.S. PATENT DOCUMENTS

| | | |
|---|---|---|
| 6,740,091 B2 | 5/2004 | Kohrs et al. |
| 6,743,206 B1 | 6/2004 | Smith |
| 6,755,841 B2 | 6/2004 | Fraser et al. |
| 6,800,084 B2 | 10/2004 | Davison et al. |
| 6,849,064 B2 | 2/2005 | Hamada |
| 6,929,606 B2 | 8/2005 | Ritland |
| 7,008,422 B2 | 3/2006 | Foley et al. |
| 7,011,660 B2 | 3/2006 | Sherman et al. |
| 7,056,321 B2 | 6/2006 | Pagliuca et al. |
| 7,083,621 B2 | 8/2006 | Shaolian et al. |
| 7,108,705 B2 | 9/2006 | Davison et al. |
| 7,144,393 B2 | 12/2006 | DiPoto et al. |
| 7,160,300 B2 | 1/2007 | Jackson |
| 7,166,107 B2 | 1/2007 | Anderson |
| 7,179,261 B2 | 2/2007 | Sicvol et al. |
| 7,188,626 B2 | 3/2007 | Foley et al. |
| 7,250,052 B2 | 7/2007 | Landry |
| 7,491,208 B2 | 2/2009 | Pond, Jr. et al. |
| 2003/0004401 A1 | 1/2003 | Ball |
| 2003/0191371 A1 | 10/2003 | Smith |
| 2004/0049207 A1 | 3/2004 | Goldfarb et al. |
| 2004/0143265 A1 | 7/2004 | Landry et al. |
| 2005/0065517 A1 | 3/2005 | Chin |
| 2005/0131408 A1 | 6/2005 | Sicvol et al. |
| 2005/0131421 A1 | 6/2005 | Anderson et al. |
| 2005/0154389 A1 | 7/2005 | Selover et al. |
| 2005/0165408 A1 | 7/2005 | Puno et al. |
| 2005/0215866 A1* | 9/2005 | Kim ............................ 600/233 |
| 2005/0215999 A1 | 9/2005 | Birkmeyer et al. |
| 2006/0200135 A1 | 9/2006 | Sherman et al. |
| 2006/0229614 A1 | 10/2006 | Foley et al. |
| 2006/0264962 A1 | 11/2006 | Chin et al. |
| 2007/0049931 A1 | 3/2007 | Justis et al. |
| 2007/0055247 A1 | 3/2007 | Jahng |
| 2007/0106123 A1 | 5/2007 | Gorek |
| 2007/0129731 A1 | 6/2007 | Sicvol et al. |
| 2007/0167954 A1 | 7/2007 | Sicvol et al. |
| 2008/0114403 A1 | 5/2008 | Kuester et al. |
| 2008/0119849 A1 | 5/2008 | Beardsley et al. |

* cited by examiner

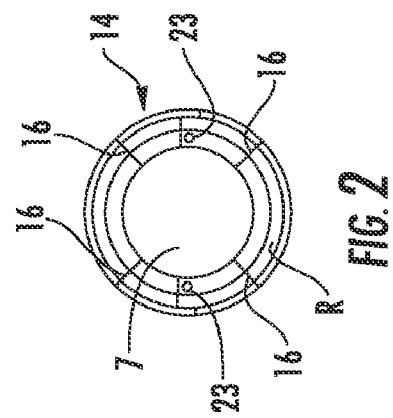
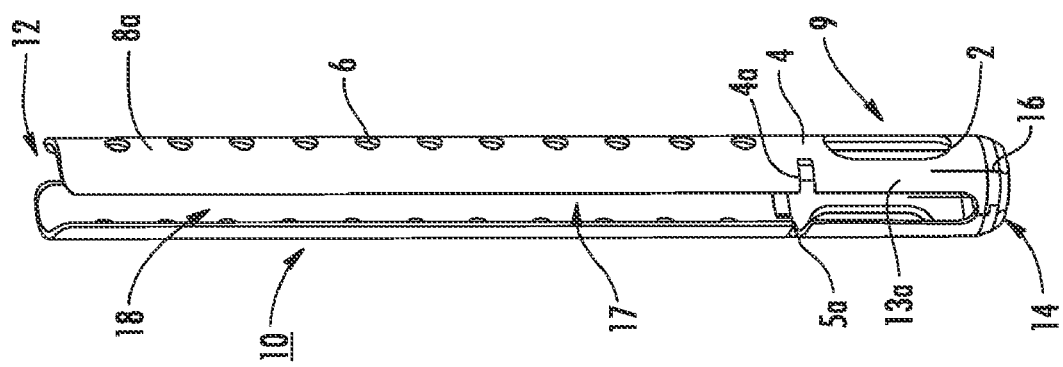
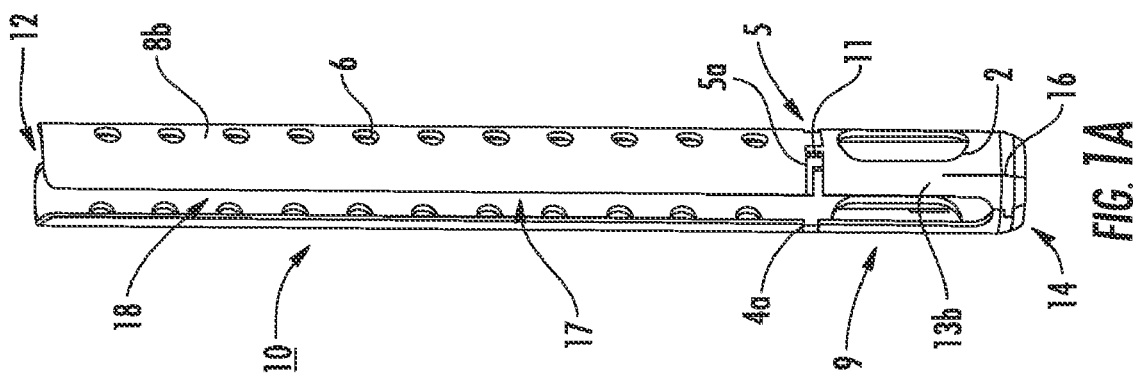

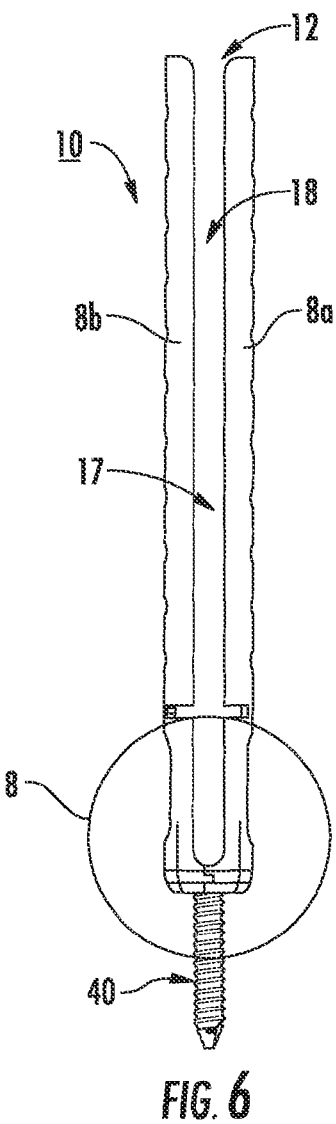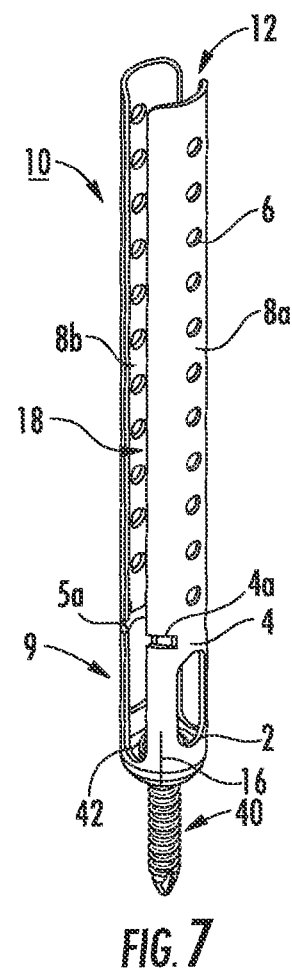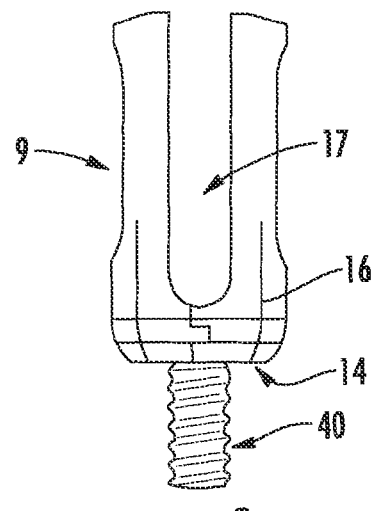
FIG. 6
FIG. 7
FIG. 8

MINIMALLY INVASIVE RETRACTOR WITH SEPARABLE BLADES AND METHODS OF USE

CROSS-REFERENCE TO RELATED APPLICATIONS

The present application is a divisional of U.S. patent application Ser. No. 12/396,098, filed Mar. 2, 2009, which claims priority to U.S. Provisional Application Ser. No. 61/032,199, filed on Feb. 28, 2008, the entire contents of both of which are incorporated herein by reference.

BACKGROUND

1. Technical Field

The present disclosure relates generally to orthopedic spine surgery and in particular to a minimally invasive retractor with separable blades and methods for use in a minimally invasive surgical procedure.

2. Background of the Technology

There has been considerable development of retractors and retractor systems that are adapted for use in less invasive procedures. Many of the recent developments are based on traditional types of surgical retractors for open procedures, predominantly table-mounted devices of various designs. These devices tend to be cumbersome and are not well adapted for use in small incisions. Standard hand-held surgical retractors are well known in the prior art and can be modified to fit the contours of these small incisions, but they require manual manipulation to maintain a desired placement, thereby occupying one hand of the physician or requiring another person to assist the physician during the procedure. Typical retractors are also positioned into the soft tissue and are levered back to hold the wound open, frequently requiring re-positioning if they dislodge, obstruct the physician's view, or interfere with access to the surgical site.

In recent years, minimally invasive surgical approaches have been applied to orthopedic surgery and more recently to spine surgery, such as instrumented fusions involving one or more vertebral bodies. Unlike minimally invasive procedures such as arthroscopic knee surgery or gallbladder surgery where the affected area is contained within a small region of the body, spinal fusion surgery typically encompasses a considerably larger region of the patient's body. In addition, arthroscopic surgery and laparoscopic surgery permit the introduction of fluid (i.e. liquid or gas) for distending tissue and creating working space for the surgeon. Surgery on the spine does not involve a capsule or space that can be so distended, instead involving multiple layers of soft tissue, bone, ligaments, and nerves. For these reasons, the idea of performing a minimally invasive procedure on the spine has only recently been approached.

By way of example, in a typical spine fusion at least two vertebral bodies are rigidly connected using screws implanted into the respective vertebral bodies with a solid metal rod spanning the distance between the screws. This procedure is not generally conducive to a minimally invasive approach. The insertion of pedicle or facet screws is relatively straightforward and can be accomplished through a minimal incision. The difficulty arises upon the introduction of a length of rod into a very small incision with extremely limited access and visibility. A single level fusion may require a 30-40 mm rod to be introduced into a 1 cm incision and a multilevel fusion may require a rod several inches long to fit into a 1 cm incision. For this reason, it is important that the minimal incision be maintained in an open and accessible condition (i.e. as wide as practicable) for introduction of the rod.

Minimally invasive surgery offers significant advantages over conventional open surgery. First, the skin incision and subsequent scar are significantly smaller. By using more than one small incision rather than one large incision, the need for extensive tissue and muscle retraction may be greatly reduced. This leads to significantly reduced post-operative pain, a shorter hospital stay, and a faster overall recovery.

Most spine implant procedures are open procedures, and while many manufacturers advertise a minimally invasive method, the procedure is typically not recommended for fusions and focuses on more common and accepted minimally invasive spine procedures such as kyphoplasty, vertebroplasty, and discectomy.

Medtronic Sofamor Danek's SEXTANT® is a minimally invasive device used for screw and rod insertion. Its shortcomings lie with how complicated the system is to use and the requirement for an additional incision for rod introduction. This system also requires that the guidance devices be rigidly fixed to the pedicle screw head in order to maintain instrument alignment and to prevent cross-threading of the set-screw. For these reasons, the surgeon cannot access the surrounding anatomy for complete preparation of the field. Nor does SEXTANT® allow for any variation in the procedure, if need be.

Depuy Spine's VIPER™ system is another minimally invasive implant and technique recommended for one or two level spine fusions. This system is less complicated than the SEXTANT®, only requiring two incisions for a unilateral, one-level fusion, but it is limited in the same way as the SEXTANT® because it also requires the instrumentation to be rigidly fixed to the pedicle screw.

Spinal Concept's PATHFINDER® and NuVasive's SPHERX® spinal system (as disclosed in U.S. Pat. No. 6,802,844), are marketed as "minimally disruptive" spine fusion implants and procedures. While they have advantages over a general "open" procedure, they do not provide all of the advantages of a truly minimally invasive approach. Their characterization as "minimally open" procedures is a result of the inherent difficulty of introducing a rod in a minimally invasive spinal procedure. In order to introduce a rod long enough to accomplish a single level fusion, these systems describe an incision long enough to accept such a rod, thereby undermining the advantages of a minimally invasive approach.

The problem of rod introduction warrants further discussion as it is the central problem in minimally invasive spinal fusions. The systems currently on the market address this issue by adding another incision, using a larger incision, or avoiding fusions greater than one level.

In order to be truly minimally invasive, a spine fusion procedure should have a minimum number of small incisions and not require significant tissue and/or muscle retraction. Furthermore, an improved approach should encompass as many variations and applications as possible thereby allowing the surgeon to adjust the procedure to accommodate the anatomy and surgical needs of the patient as presented. For instance, spinal fusions should not be limited to just one or two levels.

Therefore, a continuing need exists for an improved device, an improved system, and an improved method for performing minimally invasive spine surgery.

SUMMARY

The present disclosure relates to a device, a system, and a method for a screw-based retractor used in performing minimally invasive spine surgery. The retractor is removably attached to a pedicle bone screw that is used to guide the retractor into place and act as a point of fixation with respect to the patient. Multiple retractors may be used in conjunction with a single screw to allow retraction in multiple directions and multiple retractors may be used with multiple screws, respectively, during a single spine procedure. The retractor may be manufactured for a single use or can be sterilized and reused. Finally, the retractor may also act as a guide that will aid in the insertion of instruments and implants.

In its nominal position, the retractor extends longitudinally from the screw in a generally cylindrical shape with at least one retracting blade. Instrument holes are located perpendicular to the long axis of each retracting blade whereby a standard surgical instrument, such as a Gelpi retractor, can be used to separate the blades to retract the skin and soft tissue and maintain the field of view as well as a site for performing surgical procedures. Yet, where the retractor is connected to the pedicle screw the retractor maintains a substantially circular cross-section. Since the retractor is not permanently fixed but is removably attached to the pedicle screw, it is free to have polyaxial motion allowing the surgeon greater wound access and freedom to operate. Furthermore, polyaxial motion allows the retractor to expand medial-laterally as well as cephalad-caudally and any combination thereof. This freedom of movement proximally and non-rigid attachment distally decreases the need for retractor re-positioning during a procedure. Proximal stabilization of the retractor is possible when it is used in conjunction with either a free standing or table-mounted retractor.

The minimally invasive retractor can be designed to flex proximal or distal to the pedicle screw head. In one embodiment, the retractor has a "living hinge" and an opposing "true hinge" incorporated into the retractor's blade design. In a further embodiment, the minimally invasive retractor has a pair of living hinges. In an alternate embodiment, the minimally invasive retractor has a pair of true hinges.

As viewed along its longitudinal axis, a cross-section of the minimally invasive retractor has a generally circular configuration and provides additional stiffness. The geometry of the minimally invasive retractor provides sufficient stiffness for maintaining the opening at the surgical site.

Minimally invasive retractors having combinations of a living hinge and/or a true hinge may include at least one window that is aligned with the pedicle screw saddle and allows the insertion of instruments into the surgical site or added visualization.

The distal tip of the minimally invasive retractor is bullet shaped to aid in insertion through the soft tissue to where it will seat against the pedicle. The distal tip comprises a pair of opposed arms that may be selectively interlocked by one or more retractable pins. The distal tip may also have one or more relief features cut into it to aid in removing the retractor. Upon completion of the procedure, the retractable pin can be removed to permit separation of the opposing arms of the distal tip. In this manner, the distal tip can be separated so that the separated retractor portions (two or more) can be pulled out of the wound past the screw and rod assembly. Advantageously, by positioning the distal tip of the retractor around the head of the screw adjacent the bone, the retractor retracts soft tissue from a point adjacent or below the head of the screw, creating excellent visibility of the screw and surrounding tissue. If relief features are included, the distal tip of the retractor portions flexes to facilitate removal past the screw assembly.

BRIEF DESCRIPTION OF THE DRAWINGS

Embodiments of the presently disclosed minimally invasive retractor are described herein with reference to the accompanying drawings, wherein:

FIG. 1A is a perspective view of a minimally invasive retractor according to an embodiment of the present disclosure;

FIG. 1B is a perspective view of the minimally invasive retractor of FIG. 1A rotated 180°;

FIG. 2 is a bottom view of the minimally invasive retractor of FIGS. 1A and 1B;

FIG. 6 is a side view of a minimally invasive retractor and screw assembly including the minimally invasive retractor of FIGS. 1A and 1B;

FIG. 7 is a perspective view of the minimally invasive retractor and screw assembly of FIG. 6;

FIG. 8 is an enlarged detail view from FIG. 6 of the minimally invasive retractor and screw assembly.

DETAILED DESCRIPTION OF THE EMBODIMENTS

Figure 3:
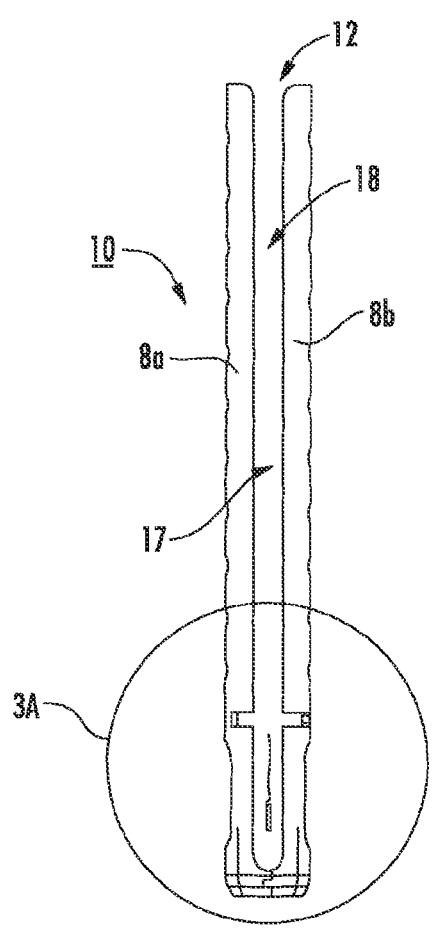
FIG. 3 is a side view of the minimally invasive retractor of FIGS. 1A and 1B.

Embodiments of the presently disclosed minimally invasive retraction device will now be described in detail with reference to the drawings wherein like reference numerals identify similar or identical elements. In the drawings and in the description which follows, the term "proximal", as is traditional, will refer to the end of the minimally invasive retraction device which is closest to the operator while the term "distal" will refer to the end of the device which is furthest from the operator.

The present disclosure relates to a device, a system, and a method for a screw-based retractor used in performing minimally invasive spine surgery. Such a device, system, and method is disclosed in U.S. patent application Ser. No. 11/528,223 filed on Sep. 26, 2006 (U.S. Patent Application Publication No. 2007/0106123), the entire contents of which are incorporated herein by reference.

Referring initially to FIGS. 1A, 1B, and 2, an embodiment of the presently disclosed minimally invasive retractor or retractor is illustrated and generally designated as 10. Retractor 10 includes an open proximal end 12 and a distal end 14. In addition, retractor 10 includes a pair of retractor blades 8a, 8b having a plurality of instrument holes 6 disposed on each of retractor blades 8a, 8b. Instrument holes 6 are configured and dimensioned to cooperate with different surgical instruments (e.g., a Gelpi retractor). A distal region 9 of retractor 10 includes an opening 7 (FIG. 2), optionally at least one slot or window 2, and a pair of arms 13a, 13b. As shown in FIG. 1A, arm 13b extends from distal end 14 to a hinged area or true hinge 5. FIG. 1B shows retractor 10 of FIG. 1A rotated 180° to illustrate arm 13a extending from distal end 14 to a flexible region or living hinge 4. Optional window 2 may be sized and configured to receive instruments therethrough and/or provide for visual inspection. Retractor blades 8a and 8b are attached to living hinge 4 and true hinge 5, respectively, to define a substantially continuous elongate member. A pair of recesses 4a is formed between retractor blade 8a and arm 13a to define living hinge 4. Arm 13b is joined to distal region 9 by a pivot pin 11 that is adapted to enable pivoting movement of retractor blade 8b relative to arm 13b during use of retractor 10, as will be discussed in detail hereinafter. A pair of recesses 5a is formed between retractor blade 8b and arm 13b to further define true hinge 5. Alternatively, retractor 10 could have two living hinges or two true hinges.

Optionally, distal end 14 may further include at least one relief region R (FIG. 2) defined by at least one slit 16 extending proximally from opening 7 (FIG. 2). Optional slit 16 may originate at window 2 and extend distally towards opening 7. It is contemplated that other arrangements of relief structures may be used to define optional relief region R and these may exist between opening 7 and window 2. Each slit 16 is a weakened portion of distal end 14. It may be a score in the material, a perforated region in the material, or another structural arrangement allowing relief region R to be radially displaced away from the centerline of retractor 10 in response to applied forces. In addition, distal end 14 has a generally convex outer surface that facilitates insertion of retractor 10 through layers of body tissue.

Retractor blades 8a, 8b and arms 13a, 13b are generally arcuate structures that cooperate to define segments of a substantially circular cross-sectional configuration for retractor 10. Preferably, each retractor blade 8a, 8b and each arm 13a, 13b have an arcuate configuration that is less than about 180° and are radially spaced apart to define a continuous slot 17 along a substantial portion of retractor 10. In addition, each retractor blade 8a, 8b and its corresponding arm 13a, 13b define a passage 18 that also extends substantially the entire length of retractor 10. Passage 18 is expandable, as will be discussed in detail hereinafter, for receiving a rod 3 (FIG. 9) therein. Retractor blades 8a, 8b and arms 13a, 13b define segments of a substantially circular ring shape in cross-section, thereby providing sufficient stiffness (i.e., rigidity) such that retractor blades 8a, 8b and arms 13a, 13b resist bending from the counter forces of the retracted tissues.

Opening 7 is located at distal end 14 of retractor 10 and is sized for receiving the shank of a threaded screw 40 (FIGS. 6-8) therethrough, but inhibiting passage of a head 42 (FIG. 7) of screw 40 so as to support screw 40 at distal end 14 of retractor 10. The interior surface of distal end 14 has a generally concave spherical geometry that is adapted to mate with head 42 of pedicle screw 40.

Figure 3A:
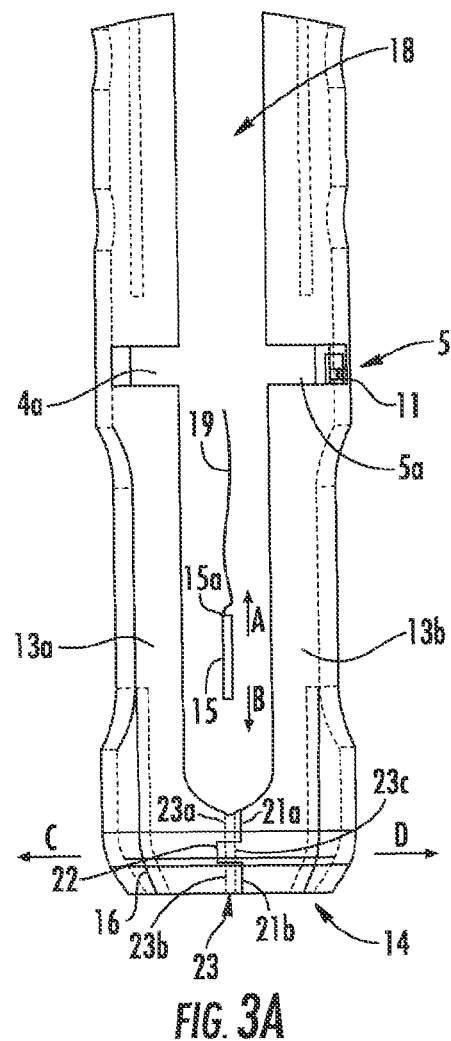
FIG. 3A is an enlarged detail view from FIG. 3 of the minimally invasive retractor.

Referring now to FIGS. 2, 3, and 3A, arms 13a and 13b are configured and dimensioned to releasably interlock to form the generally convex outer surface of distal end 14. More specifically, a pair of opposed fingers 21a, 21b are in spaced relation to each other and extend from arm 13b such that a finger 22 extending from arm 13a is received between fingers 21a, 21b to interlock arms 13a and 13b, i.e., in an interlocked position, as illustrated in FIG. 3A. A pair of substantially aligned throughbores 23a and 23b are defined through fingers 21a and 21b, respectively. In the interlocked position of arms 13a, 13b, a throughbore 23c defined through arm 22 is configured to substantially align with throughbores 23a and 23b to further define a pin receptacle 23. Pin receptacle 23 is sized for receiving a retractable pin 15 therethrough as indicated by directional arrow B, but inhibiting passage of a head 15a of retractable pin 15 so as to support retractable pin 15 at distal end 14 of retractor 10 to maintain arms 13a and 13b in the interlocked position. As shown in FIG. 3A, retractable pin 15 may be removed from interlocking receptacle 23 as indicated by directional arrow A to allow arms 13a and 13b to be separated from each other as indicated by directional arrows C and D. In the illustrated embodiment, a tether 19 is shown operably connected to pin head 15a. In use, tether 19 may be used to pull pin 15 in the direction indicated by directional arrow A to remove pin 15 from interlocking receptacle 23. In other embodiments, an elongated tool may also be used to manipulate pin 15 relative to interlocking receptacle 23. Once pin 15 is removed from interlocking receptacle 23, arms 13a and 13b may be separated from each other to facilitate disassembly of retractor 10 and thereafter removal of the separated parts of retractor 10 from the patient's body, as will be discussed in further detail hereinafter. The single interlocking receptacle 23 configuration shown in FIG. 3A is illustrative only and additional interlocking receptacles 23 may be defined at distal end 14 (see FIG. 2) for receiving a retractable pin therein to maintain arms 13a and 13b in the interlocked position.

Figure 4:
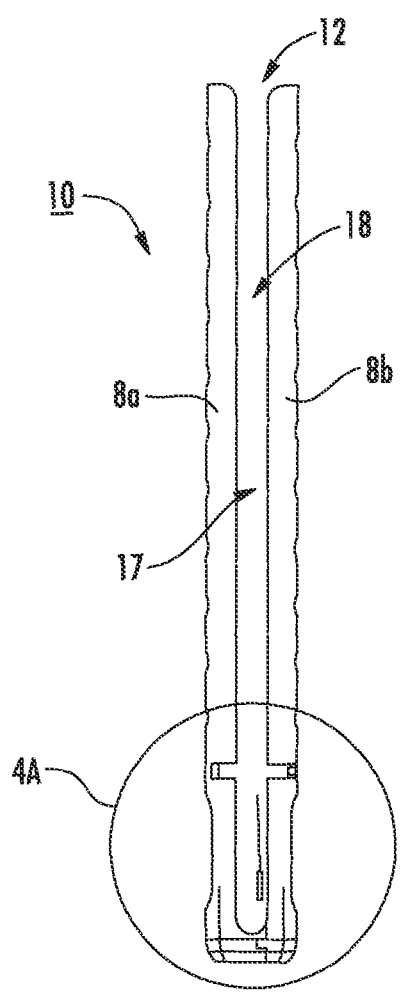
FIG. 4 is a side view of a minimally invasive retractor according to another embodiment of the present disclosure.
Figure 4A:
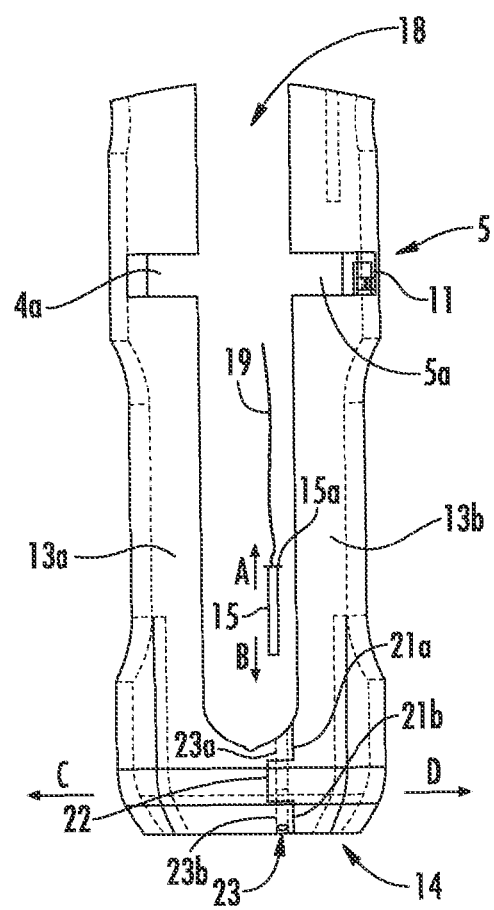
FIG. 4A is an enlarged detail view from FIG. 4 of the minimally invasive retractor.

FIGS. 4 and 4A show an embodiment of retractor 10 having at least one interlocking receptacle 23 defined substantially displaced from the centerline of retractor 10. In this embodiment, tether 19 may be utilized to remove pin 15 from interlocking receptacle 23 in substantially the same manner as discussed above with reference to FIG. 3A. By defining interlocking receptacle 23 substantially displaced from the centerline of retractor 10, removal from and/or insertion into interlocking receptacle 23 of pin 15 may be achieved without interference from structures placed along the centerline of retractor 10 during operation thereof (e.g., within slot 17 and/or through opening 7 at distal end 14) such as, for example, a pedicle screw or rod, as will be discussed in detail hereinafter. In this embodiment, optional relief features may be particularly desirable to allow flexing of the portion of the retractor extending underneath the screw assembly as removal force is applied to remove the retractor from the screw.

Figure 5:
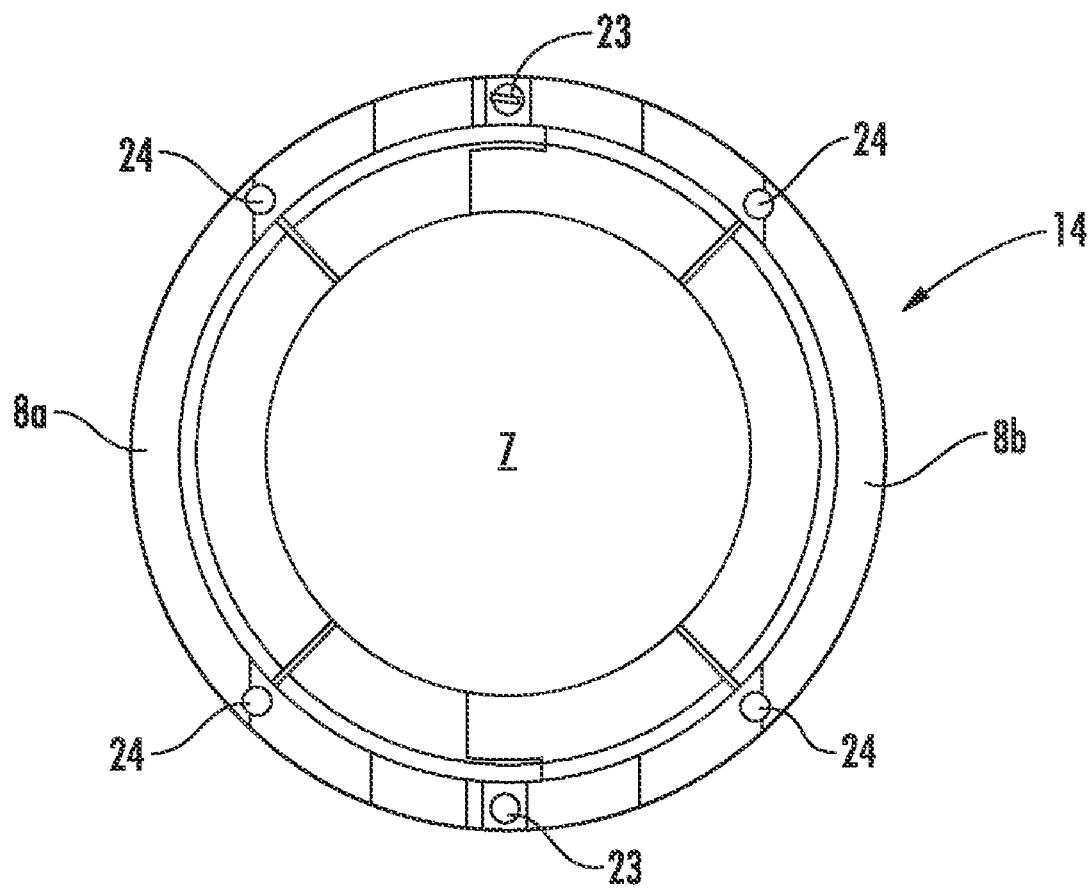
FIG. 5 is a top view of a minimally invasive retractor according to another embodiment of the present disclosure.

Referring now to FIG. 5, one or more optional tubes 24 are defined through the longitudinal cross-section of retractor blades 8a, 8b. Tubes 24 may be defined along the entire length of retractor blades 8a, 8b and are adapted to accommodate optical fiber (not shown) therethrough. The optical fiber is in optical communication with any suitable energy source known in the art (not explicitly shown) and utilized to illuminate the length of retractor 10, or any particular portion thereof, from proximal end 12 along continuous slot 17 to distal end 14. Additionally or alternatively, tubes 24 may be formed from an optically transmissive material, as is known in the art and coupled to a light source. A suitable light source may include a light emitting diode (LED).

Retractor 10 is formed from a suitable biocompatible material having the desired physical properties. That is, retractor 10 is formed of a biocompatible, sterilizable material in a suitable configuration and thickness so as to be sufficiently rigid to be held on the screw when desired during insertion and a surgical procedure and to provide retraction of tissue, and yet is sufficiently bendable to be spread apart to provide retraction and to be removed from the screw as necessary and appropriate. It is contemplated that retractor 10 may be formed from metal or plastic. Any maleable, bendable, flexible, or otherwise formable material, including metals and plastics and composites, known in the art may be used, such as titanium, titanium alloy, surgical stainless steel, nickel titanium alloys, shape memory alloy, polypropylene, polyethylene, polycarbonate, silicone, polyetheretherketone, etc. If the retractor is made from a conductive material, a non-conductive coating may be applied to the surface of retractor 10 to allow for electrical stimulation of threaded screw 40 (FIGS. 6-8) without shunting of current through retractor 10. Any suitable non-conductive dielectric material known in the art may be applied to retractor 10 to achieve this purpose. Retractor blade 8a is bendable away from the centerline of retractor 10 in response to applied forces, wherein retractor blade 8a bends at living hinge 4. Retractor blade 8b is pivotal away from the centerline of retractor 10 in response to applied forces, wherein retractor blade 8b pivots at true hinge 5. Bending and/or pivoting retractor blades 8a, 8b away from the centerline (i.e. radially outwards) creates a larger opening through retractor 10 and also acts to retract the surrounding tissue at the selected surgical site. Installation and use of retractor 10 in surgical procedures will be discussed in detail hereinafter. As will be appreciated, a malleable material is necessary if a living hinge is to be used, whereas a rigid material for the retractor blades may be used if a true hinge is used.

In FIGS. 6-8, retractor 10 is illustrated in an assembled condition with a pedicle screw 40. Pedicle screw 40 extends through opening 7 such that threads of pedicle screw 40 extend beyond distal end 14 for insertion into a target site in a bone (e.g. a vertebral body). As shown in the figures, when pedicle screw 40 is inserted in retractor 10, a head 42 (FIG. 7) of pedicle screw 40 mates with the interior geometry of distal end 14. As shown, pedicle screw 40 aligns with opening 17 between retractor blades 8a, 8b facilitating the insertion of a rod 3 (FIG. 9) into screw head 42. In addition, pedicle screw 40 is pivotable about the longitudinal axis of retractor 10 allowing retractor 10 to be attached in a first angular orientation with respect to the vertebral body, but pivotable about pedicle screw 40 increasing the amount of tissue that may be retracted using retractor 10. As will be appreciated, the pedicle screw may be cannulated such that it may be translated along a guide wire, thereby facilitating insertion of the pedicle screw and the minimally invasive retractor into the work site.

It is contemplated that any of the retractors embodied herein may be formed of a bendable resilient material such that when external spreading forces (i.e. from a Gelpi retractor or the physician's hands) are removed, the retractor blades will return towards their initial position (e.g., substantially parallel to the centerline). It is also contemplated that any of the previously disclosed retractors may be formed of a bendable non-resilient material such that when the external spreading forces are removed, the retractor blades resist returning to their initial position and remain in the retracted position.

Figure 9:
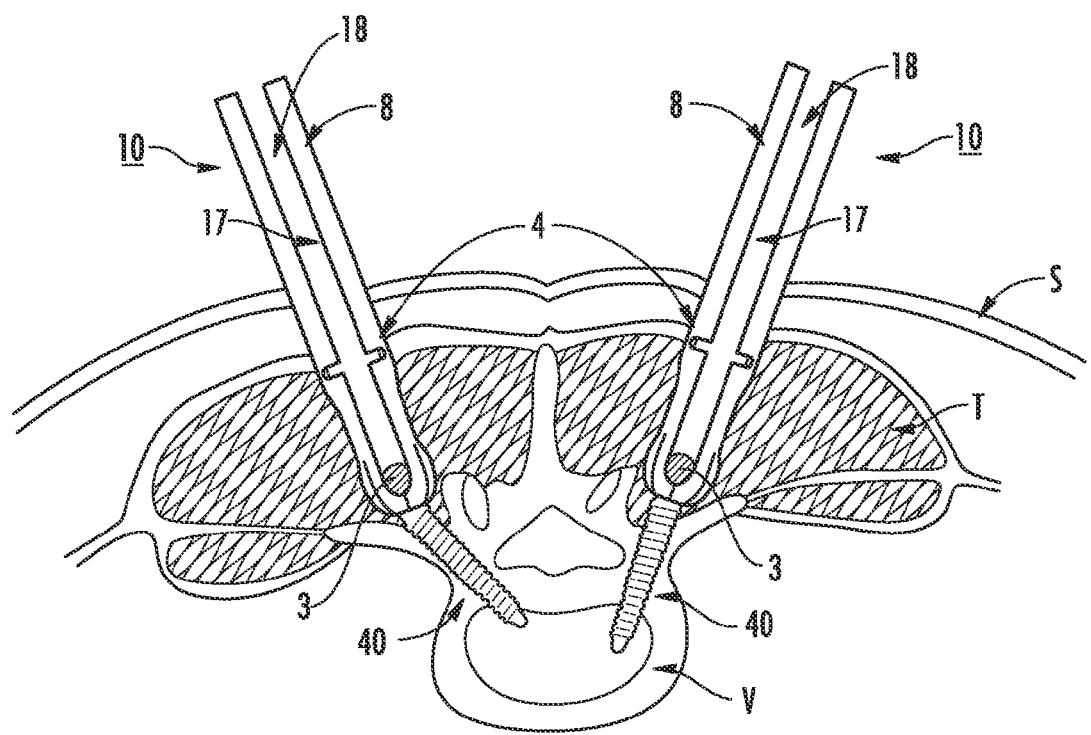
FIG. 9 is a front cross-sectional view of a vertebral body with a pair of minimally invasive retractors attached using screws with the blades in their initial position and rods positioned in the passages of the minimally invasive retractors.

A method for use of the presently disclosed system will now be described with reference to FIG. 9. Retractor 10 is assembled with pedicle screw 40 as shown in FIGS. 6-8. The assembled apparatus is inserted into an incision through the patient's skin S and muscle/fat tissue T such that pedicle screw 40 is subsequently threaded into a vertebral body V. Once the desired number of screws with retractors 10 are affixed to vertebral bodies V, retractor blades 8 are spread and/or pivoted apart to retract skin S and tissue T to create a retracted area at the target site. Rod 3 is inserted in passage 18 when passage 18 is in an expanded state (i.e., tissue has been retracted). In a preferred method, the rod may be inserted along a path from one screw head to another, possibly subcutaneously such that it may be secured to fastening regions of pedicle screws in adjacent vertebral bodies. The retractors of the present disclosure are well suited for such a technique due to the unique access provided. Once the screw-rod construct is complete, retractor 10 is removed from the patient as described above by removing the pins holding the retractor together. The separated portions may be moved away from the center line of the screw to provide clearance around the screw head, and then pulled out of the incision. This may be done by hand or with suitable gripping tools. To the extent relief regions are included, a retractor extracting tool may be used to promote flexing or separation of relief regions R to facilitate removal of the retractor 10. An example of a retractor extracting tool is described in U.S. patent application Ser. No. 11/528,223 (referenced hereinabove).

The physician may remove retractable pin 15 proximally from pin receptacle 23 using tether 19 or an elongated tool, as indicated by directional arrow A (FIG. 3A) and separate arms 13a, 13b at pin receptacle 23, thereby allowing proximal movement of the arms 13a, 13b radially away from the centerline of retractor 10, as indicated by directional arrows C and D (FIG. 3A). As such, retractor 10 is separated from pedicle screw 40 without imparting significant downward or rotational forces against the patient's body. Retractor 10 may then be removed from the patient and this process may be repeated for each installed retractor.

It is envisioned that the retractor is utilized, but not limited to, a method whereby an initial incision is made in the skin of approximately 10-15 mm in length. Surgeon preference will dictate the need for one or more stages of dilators or scalpel blades to aid in expanding the wound before introducing one or more retractors in combination with pedicle screws. Normal surgical techniques may be used to close the incision(s).

It is also contemplated that the retractor may be manufactured from medical grade metal or composites of metal. A metallic part utilizes such materials as, but not limited to, aluminum, stainless steel, nickel-titanium, titanium and alloys thereof. In addition, the parts may have a reflective or non-reflective coating to aid in increasing visibility in the wound and may have an artificial lighting feature.

It will be understood that various modifications may be made to the embodiments of the presently disclosed retraction system. Therefore, the above description should not be construed as limiting, but merely as exemplifications of embodiments. Those skilled in the art will envision other modifications within the scope and spirit of the present disclosure.

As with any surgical instrument and implant, the retractors must have the ability to be sterilized using known materials and techniques. Parts may be sterile packed by the manufacturer or sterilized on site by the user. Sterile packed parts may be individually packed or packed in any desirable quantity. For example, a sterile package may contain one or a plurality of retractors in a sterile enclosure. Alternatively, such a sterile surgical kit may also include one or a plurality of bone biopsy needles guide wires, sterile cannulated scalpels, dilators, rods, or other surgical instruments.

The blades may be made of a light transmitting material. The retractor may include a light guide system. The light guide system has an input adapter to receive light from a light source and one or more light emitting surfaces to illuminate the surgical field.

It will be understood that various modifications may be made to the embodiments of the presently disclosed retraction system. Therefore, the above description should not be construed as limiting, but merely as exemplifications of embodiments. Those skilled in the art will envision other modifications within the scope and spirit of the present disclosure.

For example, while the foregoing description has focused on spine surgery, it is contemplated that the retractors and methods described herein may find use in other orthopedic surgery applications, such as trauma surgery. Thus, where it is desired to insert a screw or pin into bone in a minimally invasive manner, or otherwise to access a surgical target site over a guidewire, the dilator, scalpel and retractors (or some of them) of the present disclosure may be used, with or without a bone screw.

Further still, it will be appreciated that the pedicle screw may be cannulated such that it may be translated along a guide wire, thereby facilitating insertion of the pedicle screw and retractor. In addition, it is contemplated that conventional insertion tools or those disclosed in U.S. patent application Ser. No. 12/104,653, filed on Apr. 17, 2008 (U.S. Patent Application Publication No. 2008/0262318), the entire contents of which are hereby incorporated by reference may be used in conjunction with the presently disclosed retractor and pedicle screws.

What is claimed is:

1. A method of retracting tissue comprising the steps of:
inserting a surgical retractor into an incision in a patient's skin;
moving first and second opposed blades of the surgical retractor away from a centerline thereof, thereby enlarging the incision;
separating the opposed blades of the surgical retractor by removing a pin from a first throughbore defined through the first blade and a second throughbore defined through the second blade and aligned with the first throughbore; and
removing the separated, opposed blades of the surgical retractor.

2. The method of claim 1, further including the step of installing a guidewire into a vertebral body.

3. The method of claim 2, wherein the step of inserting the surgical retractor further includes a cannulated bone screw extending from a distal portion of the retractor and receiving the guidewire through the screw cannulation.

4. The method of claim 1, wherein the step of inserting the surgical retractor further includes a bone screw extending from a distal portion of the retractor.

5. A method of retracting tissue, comprising the steps of:
inserting a surgical retractor into an incision in a patient's skin, the surgical retractor having a pair of opposed blades and a coupling region disposed at one end thereof, the coupling region operably coupled to the pair of opposed blades and having an opening located at a distal end thereof and at least one interlocking region adapted to permit selective separation of the pair of opposed blades;
flexing the opposed blades of the surgical retractor away from a centerline thereof, thereby enlarging the incision;
removing a pin from at least one throughbore defined through the interlocking region;
moving the surgical retractor proximally such that the coupling region separates at the at least one interlocking region away from the centerline of the surgical retractor;
separating the opposed blades of the surgical retractor; and
removing the separated, opposed blades of the surgical retractor.

6. The method of claim 5, wherein the step of removing a pin further comprises removing the pin from a throughbore defined through a first of the opposed blades and a second throughbore defined through a second of the opposed blades and aligned with the first throughbore.

7. A method of performing spine surgery comprising the steps of:
a) providing at least two retractor assemblies, each retractor assembly including a pair of opposing elongate members and at least one interlocking region located at a distal end thereof, the pair of opposing elongate members being flexibly and releasably coupled to a pedicle screw;
b) securing the first screw to a portion of a first vertebral body;
c) retracting tissue using the pair of opposing elongate members of the first retractor;
d) securing the second screw to a portion of a second vertebral body;
e) retracting tissue using the pair of opposing elongate members of the second retractor;
f) inserting a rod between the first and second screws;
g) securing the rod to the first and second screws;
h) removing a pin from at least one throughbore defined through the interlocking region;
i) moving the surgical retractor proximally such that the pair of opposing elongate members separates along the at least one interlocking region away from the centerline of the surgical retractor; and
j) removing the elongate members from the pedicle screws.

8. The method of claim 7, wherein the step of removing a pin further comprises removing the pin from a throughbore defined through a first of the elongate members and a second throughbore defined through a second of the elongate members and aligned with the first throughbore.

* * * * *